United States Patent [19]

Tinney

[11] 4,058,513

[45] Nov. 15, 1977

[54] PENTAPEPTIDES AND METHODS FOR THEIR PRODUCTION

[75] Inventor: Francis John Tinney, Ann Arbor, Mich.

[73] Assignee: Parke, Davis & Company, Detroit, Mich.

[21] Appl. No.: 699,126

[22] Filed: June 23, 1976

[51] Int. Cl.$^2$ .......................................... C07C 103/52
[52] U.S. Cl. ..................... 260/112.5 LH; 260/112.5 R
[58] Field of Search ............... 260/112.5 LH, 172.5 R

[56] References Cited

U.S. PATENT DOCUMENTS 3,796,697   3/1974   Flouret ...................... 260/112.5 LH

OTHER PUBLICATIONS

Biochem. and Biophys. Res. Comm. (1974) 57, 1248–1256.
Biochem. and Biophys. Res. Comm. (1974) 60, 406–412.

Primary Examiner—Delbert R. Phillips
Attorney, Agent, or Firm—Stephen Raines; George M. Richards; David B. Ehrlinger

[57] ABSTRACT

New pentapeptides having the formula X-R-His(benzyl)-His(benzyl)-R$^1$-Trp-R$^2$-Y wherein X is t-butoxycarbonyl or benzyloxycarbonyl, R is a single bond or Pro; R$^1$ is Ser(benzyl) or Tyr(benzyl), R$^2$ is a single bond or Ala and Y is lower alkoxy, amino, lower alkylamino or di(lower alkyl)amino with the proviso that the total number of amino acid units when R and R$^2$ are combined is one.

10 Claims, No Drawings

PENTAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected pentapeptides that are represented by the formula $$\text{X-R-His(benzyl)-His(benzyl)-R}^1\text{-Trp-R}^2\text{-Y} \qquad \text{I}$$

wherein X is t-butoxycarbonyl or benzyloxycarbonyl, R is a single bond or Pro; $R^1$ is Ser(benzyl) or Tyr(benzyl); $R^2$ is a single bond or Ala and Y is lower alkoxy, amino, lower alkylamino or di(lower alkyl)amino with the proviso that the total number of amino acid units when R and $R^2$ are combined is one.

The preferred compounds of formula I are those wherein X, R, $R^1$ and $R^2$ are as previously described and Y is methoxy, amino or ethylamino.

In formula I, the conventional symbols for amino acid residues of peptide compounds linked thereto are used and each is intended to have the following meaning: Pro, D-prolyl or L-prolyl; His(benzyl), $N^{im}$-benzyl-D-histidyl or $N^{im}$-benzyl-L-histidyl; Trp, D-tryptophyl or L-tryptophyl; Ala, D-alanyl or L-alanyl; Tyr(benzyl), D-tyrosyl(benzyl) or L-tyrosyl(benzyl) and Ser(benzyl), D-seryl(benzyl) or L-seryl(benzyl). In addition, the term "lower alkyl" is intended to mean a straight, branched or cyclic hydrocarbon moiety of up to six carbon atoms, suchd as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein X, R, $R^1$ and $R^2$ are as previously defined and Y is lower alkoxy, are produced by removing a protected pentapeptide from a resin complex of the following structure $$\text{X-R-His(benzyl)-His(benzyl)-R}^1\text{-Trp-R}^2\text{-resin} \qquad \text{II}$$

wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected pentapeptide through a methyleneoxy bridge wherein the methylene group is attached to the polymeric portion of the resin and the oxygen atom is attached to the protected pentapeptide and X, R, $R^1$ and $R^2$ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein Y is amino, lower alkylamino or di(lower alkyl)amino may be prepared by reacting compounds of the formula II wherein X, R, $R^1$ and $R^2$ are as previously defined, with ammonia, lower alkylamine or di(lower alkyl)amine.

The resin complex is suspended in a solvent, such as methanol, ethanol, dimethylformamide, etc., at a temperature of from about 0° C. to 50° C. for periods of from 12 hours to 10 days. When employing less reactive amines, the preferred solvent is dimethylformamide.

Certain of the complex resins of the formula II are prepared by coupling a protected amino acid of the formula $$\text{X-Pro-OH} \qquad \text{III}$$

wherein X is as previously defined with complex resins of the formula $$\text{His(benzyl)-His(benzyl)-R}^1\text{-Trp-R}^2\text{-resin} \qquad \text{IV}$$

wherein $R^1$ and $R^2$ are as previously defined in formula I in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about fifteen minutes to about 20 hours.

The complex resins of the formula IV are prepared by treating complex resins of the formula $$\text{t-butoxycarbonyl-His(benzyl)-His(benzyl)-R}^1\text{-Trp-}$$
$$\text{R}^2\text{-resin} \qquad \text{V}$$

wherein $R^1$ and $R^2$ are as previously defined in formula I with a large excess of trifluoroacetic acid utilizing dichloromethane as the solvent at temperatures of from 20° C. to 30° C. for about 10 minutes followed by neutralization of the trifluoroacetic acid salt with a base such as triethylamine.

Certain of the complex resins of formula II and V are prepared by coupling $$\text{X-His(benzyl)-OH}$$

to complex resins of the formula $$\text{His(benzyl)-R}^1\text{-Trp-R}^2\text{-resin} \qquad \text{VI}$$

wherein $R^1$ and $R^2$ are as previously defined in formula I using the reaction procedure described for the preparation of compounds of the formula II.

The complex resins of the formula VI are prepared by treating the complex resins of the formula $$\text{t-butoxycarbonyl-His(benzyl)-R}^1\text{-Trp-R}^2\text{-resin} \qquad \text{VII}$$

wherein $R^1$ and $R^2$ are as previously defined in formula I, with trifluoroacetic acid using the reaction procedure for the preparation of compounds of the formula IV.

Certain of the complex resins of the formula VII are prepared by coupling t-butoxycarbonyl-His(benzyl)-OH to complex resins of the formula R$^1$-Trp-R$^2$-resin      VIII wherein R$^1$ and R$^2$ are as previously defined in formula I according to the procedure used for the preparation of compounds of formula II.

The complex resins of the formula VIII are prepared by treating the complex resins of the formula t-butoxycarbonyl-R$^1$-Trp-R$^2$-resin      IX wherein R$^1$ and R$^2$ are as previously defined in formula I with trifluoroacetic acid using the reaction procedure for the preparation of compounds of the formula IV.

The complex resins of the formula IX and other useful complex resins are prepared by coupling t-butoxycarbonyl-R$^1$-OH wherein R$^1$ is as previously defined in formula I to complex resins of the formula Trp-R$^2$-resin      X wherein R$^2$ is as previously defined in formula I, according to the procedure used for the preparation of compounds of formula II.

The complex resins o the formula X are prepared by treating the complex resins of the formula t-butoxyccarbonyl-Trp-R$^2$-resin      XI wherein R$^2$ is as previously defined in formula I with trifluoroacetic acid using the reaction procedure for the preparation of compounds of the formula IV.

Certain of the complex resins of formula XI are prepared by coupling t-butoxycarbonyl-Trp-OH to complex resins of the formula Ala-resin      XII according to the procedure used for the preparation of compounds of formula II.

The complex resins of the formula XII are prepared by treating the complex resins of the formula t-butoxycarbonyl-Ala-resin      XIII with trifluoroacetic acid using the reaction procedure for the preparation of compounds of formula IV.

In accordance with this invention, compounds of the formula I, wherein X, R, R$^1$ and R$^2$ are as previously described and Y is amino, lower alkylamino or di(lower alkyl)amino are prepared by reacting a compound of the formula I wherein Y is alkoxy, preferably methoxy, with ammonia, lower alkylamine or di(lower alkylamine).

The reactions are conducted at temperatures of from about 5° C. to 100° C. for from three hours to four days, preferably about room temperature. Generally, a large excess of amine is used (over five fold). The reaction is usually carried out in a non-reactive solvent, such as a lower alkyl alcohol, preferably methanol of ethanol, an ether such as tetrahydrofuran or dioxane, dimethylformamide or mixtures thereof.

In addition, in accordance with this invention, compounds of the formula I, wherein X, R, R$^1$ and R$^2$ are as previously defined and Y is amino, lower alkylamino or di(lower alkyl)amino are prepared by reacting a compound of the formula X-R-His(benzyl)-His(benzyl)-R$^1$-Trp-R$^2$-N$_3$      XIV with ammonia, lower alkylamine or di(lower alkyl)amine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of the amine, about 10 percent, is preferred. When X is t-butoxycarbonyl, care should be taken to avoid the presence of a large excess of acid.

The azide compounds of the formula XIV are normally prepared in situ by reacting a peptide hydrazide of the formula X-R-His(benzyl)-His(benzyl)-R$^1$-Trp-R$^2$-NHNH$_2$      XV wherein X, R, R$^1$ and R$^2$ are as defined in formula I with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° C. and 0° C. following the in site formation of the azide of formula XIV and prior to the further reaction of the peptide azide with the appropriate amine to form certain pentapeptides of formula I, a tertiary amine such as triethylamine is added to the reaction mixture to neutralize the acid used.

The compounds of formula XV are prepared by reacting a compound of formula I wherein Y is methoxy with hydrazine hydrate in methanol.

Compounds of the formula I wherein X, R, R$^1$ and R$^2$ are as described in formula I and Y is amino, lower alkylamino or di(lower alkyl)amino are prepared by coupling a compound of the formula X-R-His(benzyl)-His(benzyl)-R$^1$-Trp-R$^2$-OH      XVI with ammonia, a lower alkylamine or a di(lower alkyl) amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° C. to 50° C., preferably room temperature for periods of from ten hours to five days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula XVI are prepared by the hydrolysis of a compound of formula I wherein X, R, R$^1$ and R$^2$ are as previously defined and Y is lowere alkoxy. The reaction is conducted at temperatures of from 20° C. to 30° C. using about 0.5 ml. of two normal aqueous sodium hydroxide solution and 10 ml. of solvent, usually water or an alcohol such as methanol, for each millimole of ester. The compound of formula XVI is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Pentapeptides of this invention were screened for LRF antagonist activity in vitro using rat anterior pituitary cell cultures as described by Vale et. al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

ACTIVITY TABLE FOR IN VITRO TEST
IN RAT ANTERIOR PITUITARY
CELL CULTURES

| | Molar Conc. | LH Value ng/ml. | % LH Release Inhibition |
|---|---|---|---|
| N$^\alpha$-t-Butoxycarbonyl-N$^{im}$- | 1×10$^{-6}$ | 10.05 | 91 |
| benzyl-L-histidyl-N$^{im}$- | 6×10$^{-7}$ | 11.58 | 86 |
| benzyl-L-histidyl-O-benzyl- | 3×10$^{-7}$ | 20.87 | 58 |
| L-seryl-L-tryptophyl-D- | 1×10$^{-7}$ | 38.15 | 7 |
| alanine methyl ester | 6×10$^{-8}$ | 41.58 | 0 |
| LRF Control | 3.5×10$^{-10}$ | 40.46 | |
| Saline Control | | 6.96 | |
| N$^\alpha$-Benzyloxycarbonyl-N$^{im}$- | 6×10$^{-7}$ | 19.89 | 83 |
| benzyl-L-histidyl-N$^{im}$- | 3.5×10$^{-7}$ | 30.03 | 64 |
| benzyl-L-histidyl-O-benzyl- | 2×10$^{-7}$ | 30.84 | 62 |
| L-tyrosyl-L-tryptophyl-D- | 1×10$^{-7}$ | 36.33 | 52 |
| alanine methyl ester | 6×10$^{-8}$ | 41.17 | 43 |
| LRF Control | 3.5×10$^{-10}$ | 64.13 | |
| Saline Control | | 10.79 | |
| N$^\alpha$-Benzyloxycarbonyl-N$^{im}$- | 2.5×10$^{-7}$ | 15.02 | 95 |
| benzyl-L-histidyl-N$^{im}$- | 1×10$^{-7}$ | 24.45 | 76 |
| benzyl-L-histidyl-O-benzyl- | 5×10$^{-8}$ | 34.05 | 57 |
| L-seryl-L-tryptophyl-L- | 2.5×10$^{-8}$ | 45.43 | 35 |
| alanine N-ethylamide | | | |
| LRF Control | 5×10$^{-10}$ | 63.01 | |
| Saline Control | | 12.22 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the pentapeptides of this invention are useful in controlling ovulation and in restricting fertility.

The invention is illustrated by the following examples.

EXAMPLE 1

N$^\alpha$-t-Butoxycarbonyl-N$^{im}$-benzyl-L-histidyl-N$^{im}$-benzyl-L-histidyl-O-benzyl-L-seryl-L-tryptophyl-D-alanine methyl ester N$^\alpha$-t-Butoxycarbonyl-N$^{im}$-benzyl-L-histidyl-N$^{im}$-benzyl-L-histidyl-O-benzyl-L-seryl-L-tryptophyl-D-alanine resin, 6.8 g., is stirred with 50 ml. of triethylamine in 500 ml. of methanol at room temperature for two days. After filtration and evaporation, the crude above named product is chromatographed on silica gel with 10% methanol in benzene; 2.0 g. as a sesquihydrate; m.p. 75°–80° C.

General Procedure for the Solid Phase Synthesis of Peptide Resins

The peptide resin is obtained by attaching an α-amino protected amino acid to a resin (usually a chloromethylated resin which is commercially available from Lab Systems, Inc., San Mateo, California). The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart "Solid Phase Peptide Synthesis", W. H. Freeman and Co., 1969.

Each cycle of the procedure follows the scheme:
1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. Fifteen to thirty minutes agitation with the α-amino-protected amino acid in 20% molar excess (based on the resin nitrogen anaylsis). In an alternate method, a 4-fold excess of the α-amino-protected amino acid is agitated with the resin for 15 minutes and the excess recovered by draining the solution from the reactor.
6. Addition of dicyclohexylcarbodiimide at least equivalent to the α-amino-protected amino acid in Step 5 in dichloromethane followed by agitation for 4 to 20 hours. In the alternate method, a 3.3-fold excess of dicyclohexylcarbodiimide is used relative to the α-amino-protected amino acid resin.
7. Three washes with dichloromethane.

N$^\alpha$-t-Butoxycarbonyl-N$^{im}$-benzyl-L-histidyl-N$^{im}$-benzyl-L-histidyl-O-benzyl-L-seryl-L-tryptophyl-D-alanine resin is obtained from 16.3 g. (0.011 mol) of N$^\alpha$-t-butoxycarbonyl-D-alanine resin by successive couplings according to the above General Procedure with (1) 5.3 g. (0.017 mol) of N$^\alpha$-t-butoxy-carbonyl-L-tryptophan and 3.3 g (0.016 mol) of dicyclohexylcarbodiimide, (2) 4.7 g. (0.016 mol) of N$^\alpha$-t-butoxycarbonyl-O-benzyl-L-serine and 3.3 g. of dicyclohexylcarbodiimide, (3) using 15.3 g. of resin from 23 g. obtained in Step 2, 3.9 g. (0.011 mol) of N$^\alpha$-t-butoxycarbonyl-N$^{im}$-benzyl-L-histidine and 2.3 g. (0.011 mol) of dicyclohexylcarbodiimide and (4) using 7.0 g. of resin from 14.1 g. obtained in Step 3. 3 g. (0.0087 mol) of N$^\alpha$-t-butoxycarbonyl-N$^{im}$-benzyl-L-histidine and 3 g. (0.015 mol) of dicyclohexylcarbodiimide.

EXAMPLE 2

$N^\alpha$-t-Butoxycarbonyl-$N^{im}$-benzyl-L-histidyl-$N^{im}$-benzyl-L-histidyl-O-benzyl-L-seryl-L-tryptophyl-D-alanine N-ethylamide The methyl ester of Example 1, 0.3 g., is treated with 5 ml. of ethylamine in 200 ml. of methanol at room temperature for three days. The above named product is isolated after evaporation of the volatile components and the chromatographing of the residue on silica gel with 10 percent methanol in benzene; 0.23 g. as a hemihydrate; m.p. 92°-98° C.

EXAMPLE 3

$N^\alpha$-Benzyloxycarbonyl-$N^{im}$-benzyl-L-histidyl-$N^{im}$-benzyl-L-histidyl-O-benzyl-L-seryl-L-tryptophyl-D-alanine methyl ester $N^\alpha$-Benzyloxycarbonyl-$N^{im}$-benzyl-L-histidyl-$N^{im}$-benzyl-L-histidyl-O-benzyl-L-seryl-L-tryptophyl-D-alanine resin, 8.3 g., is treated with 20 ml. of triethylamine and 200 ml. of methanol at room temperature for two days. The suspension is filtered and the solvent evaporated. The residual oil is chromatographed on silica gel with 20 percent methanol in benzene to give the above named product; 2.5 g; m.p. 82°-87° C.

$N^\alpha$-Benzyloxycarbonyl-$N^{im}$-benzyl-L-histidyl-$N^{im}$-benzyl-L-histidyl-O-benzyl-L-seryl-L-tryptophyl-D-alanine resin is obtained using the procedure given in Example 1 and by substituting in Step 4, 1.9 g. (0.005 mol) of $N^\alpha$-benzyloxycarbonyl-$N^{im}$-benzyl-L-histidine (which must be dissolved in dimethylformamide rather than in dichloromethane) and 1.1 g. (0.005 mol) of dicyclohexylcarbodiimide with 9.0 g. of $N^\alpha$-t-butoxycarbonyl-$N^{im}$-benzyl-L-histidyl-O-benzyl-seryl-L-tryptophyl-D-alanine resin. The yield is 8.3 g. of resin.

EXAMPLE 4

$N^\alpha$-Benzyloxycarbonyl-$N^{im}$-benzyl-L-histidyl-$N^{im}$-benzyl-L-histidyl-O-benzyl-L-seryl-L-tryptophyl-D-alanine N-ethylamide The methyl ester of Example 3, 0.4 g., is treated with 5 ml. of ethylamine in 100 ml. of methanol at room temperature for two days. After evaporation, the residue is chromatographed on silica gel with chloroform-methanol-water (60:30:5) yielding the above named product; 0.3 g. as a hemihydrate; m.p. 80°-84° C.

EXAMPLE 5

$N^\alpha$-Benzyloxycarbonyl-$N^{im}$-benzyl-L-histidyl-$N^{im}$-benzyl-L-methyl ester $N^\alpha$-Benzyloxycarbonyl-$N^{im}$-benzyl-L-histidyl-$N^{im}$-benzyl-L-histidyl-O-benzyl-L-tyrosyl-L-tryptophyl-D-alanine resin, 15.8 g., is treated with 20 ml. of triethylamine and 200 ml. of methanol. After filtration and evaporation the crude above named product is chromatographed on silica gel with 20% methanol in chloroform; 1.0 g. as a hemihydrate; m.p. 85°-90° C.

$N^\alpha$-Benzyloxycarbonyl-$N^{im}$benzyl-L-histidyl-$N^{im}$-benzyl-L-histidyl-O-benzyl-L-tyrosyl-L-tryptophyl-D-alanine resin is obtained according to the General Procedure of Example 1 from 30 g. (0.0198 mol) of $N^\alpha$-t-butoxycarbonyl-D-alanine resin by successive couplings with (1) 9.1 g. (0.03 mol) of $N^\alpha$-t-butoxycarbonyl-L-tryptophan and 6.8 g. (0.03 mol) of dicyclohexylcarbodiimide, (2) 11.1 g. (0.03 mol) of $N^\alpha$-t-butoxycarbonyl-O-benzyl-L-tyrosine and 6.8 g. of dicyclohexylcarbodiimide, (3) using 95 g. of wet resin cake from 143 g. obtained in Step 2, 7.0 g. (0.02 mol) of $N^\alpha$-t-butoxycarbonyl-$N^{im}$-benzyl-L-histidine and 4.6 g. (0.02 mol) of dicyclohexylcarbodiimide and (4) using 21 g. of resin cake from 41.9 g. obtained in Step 3, 4.0 g. (0.01 mol) of $N^\alpha$-benzyloxycarbonyl-$N^{im}$-benzyl-L-histidine (dissolved in dimethylformamide) and 2.3 g. (0.01 mol) of dicyclohexylcarbodiimide.

$N^\alpha$-t-Butoxycarbonyl-D-alanine resin is prepared by mixing 100 g. of 1% chloromethylated resin, 35 g. (0.185 mol) $N^\alpha$-t-butoxycarbonyl-D-alanine and 18.5 g. (0.183 mol) of triethylamine in 500 ml. of ethanol. The mixture is refluxed for three days, filtered, the resin washed with ethanol, water, methanol and ether and dried; 102.1 g. Analysis for nitrogen shows 0.00066 mol per gram.

EXAMPLE 6

$N^\alpha$-Benzyloxycarbonyl-$N^{im}$-benzyl-L-histidyl-$N^{im}$-benzyl-L-histidyl-O-benzyl-L-tyrosyl-L-tryptophyl-D-alanine N-ethylamide The methyl ester of Example 5, 0.4 g., is treated with 5 ml. of ethylamine in 150 ml. of methanol at room temperature for 4 days. After removal of the volatile components, the above named product is obtained, 0.2 g. as a monohydrate; m.p. 100°-105° C.

EXAMPLE 7

$N^\alpha$-Benzyloxycarbonyl-$N^{im}$-benzyl-L-histidyl-$N^{im}$-benzyl-L-histidyl-O-benzyl-L-seryl-L-tryptophyl-L-analine methyl ester $N^\alpha$-Benzyloxycarbonyl-$N^{im}$-benzyl-L-histidyl-$N^{im}$-benzyl-L-histidyl-O-benzyl-L-seryl-l-tryptophyl-L-alanine resin, 9.5 g., is treated with methanol, 200 ml., and triethylamine, 20 ml., at room temperature for two days, filtered and the filtrate evaporated. The crude above named product is chromatographed on silica gel with benzene-chloroform (80:20) to give 0.7 g., m.p. 115°-120° C.

The $N^\alpha$-benzyloxycarbonyl-$N^{im}$-benzyl-L-histidyl-$N^{im}$-benzyl-L-histidyl-O-benzyl-L-seryl-L-tryptophyl-L-alanine resin is obtained by the general procedure of Example 1 using 20 g. (0.0128 mol) of $N^\alpha$-t-butoxycarbonyl-L-alanine resin with (1) 6.1 g. (0.02 mol) of $N^\alpha$-t-butoxycarbonyl-L-tryptophan and 4.6 g. (0.022 mol) of dicyclohexylcarbodiimide, (2) 5.6 g. (0.019 mol) of $N^\alpha$-t-butoxycarbonyl-O-benzyl-L-serine and 4.6 g. (0.022 mol) of dicyclohexylcarbodiimide, (3) 6.6 g. (0.019 mol) of $N^\alpha$-t-butoxycarbonyl-$N^{im}$-benzyl-L-histidine and 4.6 g. (0.022 mol) of dicyclohexylcarbodiimide and finally (4) with 23.3 g. of undried resin containing methylene chloride obtained in Step 3, 2.7 g. (0.007 mol) of $N^\alpha$-benzyloxycarbonyl-$N^{im}$-benzyl-L-histidine and 2.3 g. (0.011 mol) of dicyclohexylcarbodiimide.

$N^\alpha$-t-Butoxycarbonyl-L-alanine resin is prepared by mixing 50 g. of 1% chloromethylated resin, 17.5 g. (0.093 mol) $N^\alpha$-t-butoxycarbonyl-L-alanine and 9.3 g. (0.093 mol) of triethylamine in 500 ml. of ethanol. The mixture is refluxed for two days, filtered, the resin washed with ethanol, water, methanol and ether and dried; 51.3 g. Analysis for nitrogen shows 0.00064 mol per gram.

EXAMPLE 8

N$^\alpha$-benzyloxycarbonyl-N$^{im}$-benzyl-L-histidyl-N$^{im}$-benzyl-L-histidyl-O-benzyl-L-seryl-L-tryptophyl-L-alanine N-ethylamide The methyl ester from Example 7, 0.4 g., is reacted with 5 ml. of ethylamine in a mixture of 140 ml. of methanol and 10 ml. of dimethylformamide at room temperature for 16 hours. The above named product, 0.23 g., is obtained as a hydrate after evaporation and recrystallization from dimethylformamide-ether; m.p. 150°–155° C.

EXAMPLE 9

N$^\alpha$-t-Butoxycarbonyl-L-prolyl-N$^{im}$-benzyl-L-histidyl-N$^{im}$benzyl-L-histidyl-O-benzyl-L-tyrosyl-D-tryptophan methyl ester N$^\alpha$-t-Butoxycarbonyl-L-prolyl-N$^{im}$-benzyl-L-histidyl-N$^{im}$-benzyl-L-histidyl-O-benzyl-L-tyrosyl-D-tryptophan resin, 6.6 g., is treated with methanol, 100 ml., and triethylamine, 10 ml., at room temperature for five days, filtered and the filtrate evaporated. The crude above named product is chromatographed on silica gel with benzene-methanol (95:5) to give 0.9 g.; m.p. 85°–90° C.

The N$^\alpha$-t-butoxycarbonyl-L-prolyl-N$^{im}$-benzyl-L-histidyl-N$^{im}$-benzyl-L-histidyl-O-benzyl-L-tyrosyl-D-tryptophan resin is obtained by the General Procedure of Example 1 using 11 g. (0.0052 mol) of N$^\alpha$-t-butoxycarbonyl-D-tryptophan resin with (1) 3 g. (0.008 mol) of N$^\alpha$-t-butoxycarbonyl-O-benzyl-L-tyrosine and 1.8 g. (0.0087 mol) of dicyclohexylcarbodiimide, (2) 2.8 g. (0.008 mol) of N$^\alpha$-t-butoxycarbonyl-N$^{im}$-benzyl-L-histidine and 1.8 g. (0.0087 mol) of dicyclohexylcarbodiimide, (3) 2.8 g. (0.008 mol) of N$^\alpha$-t-butoxycarbonyl-N$^{im}$-benzyl-L-histidine and 1.8 g. (0.0087 mol) of dicyclohexylcarbodiimide and finally (4) with 6.7 g. of resin from 13.5 g. obtained in Step 3, 0.9 g. (0.004 mol) of N$^\alpha$-t-butoxycarbonyl-L-proline and 0.9 g. (0.0044 mol) of dicyclohexylcarbodiimide.

Example 10

N$^\alpha$-t-Butoxycarbonyl-L-prolyl-N$^{im}$-benzyl-L-histidyl-N$^{im}$-benzyl-L-histidyl-O-benzyl-L-seryl-D-tryptophan methyl ester N$^\alpha$-t-Butoxycarbonyl-L-prolyl-N$^{im}$-benzyl-L-histidyl-N$^{im}$-benzyl-L-histidyl-O-benzyl-L-seryl-D-tryptophan resin, 6.5 g., is treated with methanol, 100 ml., and triethylamine, 10 ml., at room temperature for five days, filtered and the filtrate evaporated. The crude above named product is chromatographed on silica gel with benzene-methanol (95:5) to give 0.8 g. as a hemihydrate; m.p. 75°–80° C.

The N$^\alpha$-t-butoxycarbonyl-L-prolyl-N$^{im}$-benzyl-L-histidyl-N$^{im}$-benzyl-L-histidyl-O-benzyl-L-seryl-D-tryptophan resin is obtained by the General Procedure of Example 1 using 11 g. (0.005 mol) of N$^\alpha$-t-butoxycarbonyl-D-tryptophan resin with (1) 2.4 g. (0.008 mol) of N$^\alpha$-t-butoxycarbonyl-O-benzyl-L-serine and 1.7 g. (0.008 mol) of dicyclohexylcarbodiimide, (2) 2.8 g. (0.008 mol) of N$^\alpha$-t-butoxycarbonyl-N$^{im}$-benzyl-L-histidine and 1.8 g. (0.0087 mol) of dicyclohexylcarbodiimide, (3) 2.8 g. (0.008 mol) of N$^\alpha$-t-butoxycarbonyl-N$^{im}$-benzyl-L-histidine and 1.8 g. (0.0087 mol) of dicyclohexylcarbodiimide and finally 4) with 6.5 g. of resin from 13 g. obtained in Step 3, 0.9 g. (0.004 mol) of N$^\alpha$-t-butoxycarbonyl-L-proline and 0.9 g. (0.0044 mol) of dicyclohexylcarbodiimide.

N$^\alpha$-t-Butoxycarbonyl-D-tryptophan resin is prepared by mixing 20 g. of 1% chloromethylated resin, 7.7 g. (0.025 mol) N$^\alpha$-t-butoxycarbonyl-D-tryptophan and 2.4 g. (0.023 mol) of triethylamine in 250 ml. of ethanol. The mixture is refluxed for four days, filtered, the resin washed with ethanol, water, methanol and ether and dried; 22 g. Analysis for nitrogen shows 0.00047 mol per gram.

EXAMPLE 11

N$^\alpha$-t-Butoxycarbonyl-L-prolyl-N$^{im}$-benzyl-L-histidyl-N$^{im}$-benzyl-L-histidyl-O-benzyl-L-seryl-D-tryptophanamide The methyl ester of Example 10, 0.3 g., is reacted with 100 ml. of methanol saturated with ammonia at room temperature for one day. After removal of the methanol and ammonia by evaporation, the crude above named product is chromatographed on silica gel using benzene-methanol (90:10) to give 0.21 g. of the product; m.p. 95°–100° C.

EXAMPLE 12

N$^\alpha$-t-Butoxycarbonyl-L-prolyl-N$^{im}$-benzyl-L-histidyl-N$^{im}$-benzyl-L-histidyl-O-benzyl-L-seryl-D-tryptophan N-ethylamide The methyl ester from Example 10, 0.3 g., is reacted with 10 ml. of ethylamine in 100 ml. methanol for seven days. The above named product, 0.22 g., is obtained as a hemihydrate after evaporation and chromatography on silica gel using benzene-methanol (90:10); m.p. 97°–102° C.

EXAMPLE 13

N$^\alpha$-t-Butoxycarbonyl-L-prolyl-N$^{im}$-benzyl-L-histidyl-N$^{im}$-benzyl-L-histidyl-O-benzyl-L-tyrosyl-D-tryptophanamide The methyl ester of Example 9, 0.3 g., is reacted with 100 ml. of methanol saturated with ammonia at room temperature for four days. After removal of the methanol and ammonia by evaporation, the crude residue is chromatographed on silica gel using benzene-methanol (90:10) to give 0.19 g. of the above named product as a hemi-hydrate, m.p. 105°–110° C.

EXAMPLE 14

N$^\alpha$-t-Butoxycarbonyl-L-prolyl-N$^{im}$-benzyl-L-histidyl-N$^{im}$-benzyl-L-histidyl-O-benzyl-L-tyrosyl-D-tryptophan N-ethylamide The methyl ester from Example 9, 0.2 g., is reacted with 10 ml. of ethylamine in 100 ml. of methanol for one day. The above named product, 0.07 g., is obtained as a hemihydrate after evaporation and chromatography on silica gel using benzene-methanol (90:10); m.p. 95°–100° C.

I claim:
1. A pentapeptide of the formula

wherein X is t-butoxycarbonyl or benzyloxycarbonyl, R is a single bond or Pro; R$^1$ is Ser(benzyl) or Tyr(benzyl); R$^2$ is a single bond or Ala and Y is lower alkoxy, amino, lower alkylamino or di(lower alkyl)amino with the proviso that the total number of amino acid units when R and R² are combined is one.

2. The pentapeptides of claim 1 wherein R, R¹ and R² are as described in claim 1 and Y is methoxy, amino or ethylamino.

3. The pentapeptide of claim 1 having the name N$^\alpha$-t-butoxycarbonyl-N$^{im}$-benzyl-L-histidyl-N$^{im}$-benzyl-L-histidyl-O-benzyl-L-seryl-L-tryptophyl-D-alanine methyl ester.

4. The pentapeptide of claim 1 having the name N$^\alpha$-t-butoxycarbonyl-N$^{im}$-benzyl-L-histidyl-N$^{im}$-benzyl-L-histidyl-O-benzyl-L-seryl-L-tryptophyl-D-alanine N-ethylamide.

5. The pentapeptide of claim 1 having the name N$^\alpha$-benzyloxycarbonyl-N$^{im}$-benzyl-L-histidyl-N$^{im}$-benzyl-L-histidyl-O-benzyl-L-seryl-L-tryptophyl-D-alanine methyl ester.

6. The pentapeptide of claim 1 having the name N$^\alpha$-benzyloxycarbonyl-N$^{im}$-benzyl-L-histidyl-N$^{im}$-benzyl-L-histidyl-O-benzyl-L-seryl-L-tryptophyl-D-alanine N-ethylamide.

7. The pentapeptide of claim 1 having the name N$^\alpha$-benzyloxycarbonyl-N$^{im}$-benzyl-L-histidyl-N$^{im}$-benzyl-L-histidyl-O-benzyl-L-tyrosyl-L-tryptophyl-D-alanine methyl ester.

8. The pentapeptide of claim 1 having the name N$^\alpha$-benzyloxycarbonyl-N$^{im}$-benzyl-L-histidyl-N$^{im}$-benzyl-L-histidyl-O-benzyl-L-tyrosyl-L-tryptophyl-D-alanine N-ethylamide.

9. The pentapeptide of claim 1 having the name N$^\alpha$-benzyloxycarbonyl-N$^{im}$-benzyl-L-histidyl-N$^{im}$-benzyl-L-histidyl-O-benzyl-L-seryl-L-tryptophyl-L-alanine methyl ester.

10. The pentapeptide of claim 1 having the name N$^\alpha$-benzyloxycarbonyl-N$^{im}$-benzyl-L-histidyl-N$^{im}$-benzyl-L-histidyl-O-benzyl-L-seryl-L-tryptophyl-L-alanine N-ethylamide.

* * * * *